United States Patent
Brock et al.

(10) Patent No.: US 6,432,112 B2
(45) Date of Patent: *Aug. 13, 2002

(54) ARTICULATED APPARATUS FOR TELEMANIPULATOR SYSTEM

(75) Inventors: David L. Brock, Natick; Woojin Lee, Cambridge, both of MA (US)

(73) Assignee: Brock Rogers Surgical, Inc., Norwood, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/827,503

(22) Filed: Apr. 6, 2001

Related U.S. Application Data

(63) Continuation of application No. 09/746,853, filed on Dec. 21, 2000, which is a division of application No. 09/375,666, filed on Aug. 17, 1999, now Pat. No. 6,197,017, which is a continuation of application No. 09/028,550, filed on Feb. 24, 1998, now abandoned.

(51) Int. Cl.$^7$ ................................................ A61B 19/00
(52) U.S. Cl. ........................ 606/130; 606/1; 606/630; 414/5; 414/730
(58) Field of Search ................................ 606/130, 1, 88, 606/630; 414/729, 730, 732, 737, 5, 7; 74/469, 89.22; 901/9, 21, 15, 27, 25, 48; 318/658.19, 567, 571; 254/256, 393

(56) References Cited

U.S. PATENT DOCUMENTS

| | | |
|---|---|---|
| 2,819,111 A | 1/1958 | Cozzens |
| 2,978,118 A | 4/1961 | Goertz et al. |
| 3,587,872 A | 6/1971 | Pauly |
| 3,631,737 A | 1/1972 | Wells |
| 3,694,021 A | 9/1972 | Mullen |
| 3,866,966 A | 2/1975 | Skinner, II |
| 3,877,780 A | 4/1975 | Taylor |
| 3,976,206 A | 8/1976 | Flateau |
| 4,066,141 A | 1/1978 | Elvin |
| 4,218,173 A | 8/1980 | Coindet et al. |
| 4,233,837 A | 11/1980 | Canfield |
| 4,246,661 A | 1/1981 | Pinson |
| 4,259,876 A * | 4/1981 | Belyanin et al. ............... 74/469 |
| 4,287,759 A | 9/1981 | Cooper |
| 4,566,843 A | 1/1986 | Iwatsuka et al. |
| 4,655,673 A | 4/1987 | Hawkes |
| 4,784,010 A | 11/1988 | Wood et al. |
| 4,806,066 A * | 2/1989 | Rhodes et al. ............... 414/729 |
| 4,854,808 A * | 8/1989 | Bruno ......................... 414/680 |
| 4,865,376 A | 9/1989 | Leaver et al. |

(List continued on next page.)

FOREIGN PATENT DOCUMENTS

| | | |
|---|---|---|
| EP | 0776738 A2 | 6/1997 |
| WO | WO98/25666 | 6/1998 |
| WO | WO00/60521 | 10/2000 |

OTHER PUBLICATIONS

Tokuji Okada, "Computer Control of Multijointed Finger System for Precise Object–Handling", May/Jun. 1982, IEEE Transactions on Systems, Man, and Cybernetics, vol. SMC–12, No. 3., pp. 289–299.

Tokuji Okada, "A Versatile End–Effector With Flexible Fingers", Winter 1979, Robotics Age, pp. 31–39.

Primary Examiner—Pedro Philogene

(57) ABSTRACT

An articulated apparatus is disclosed that includes a first link member, a second link member, and a third link member. The second link member is coupled to the first link member at a proximal end of the second link member by a first joint having a first axis of rotation. The third link member is coupled to a distal end of the second link member by a second joint. The movement of the third link member with respect to the second link member is governed by at least one tendon that passes through the first axis of rotation of the first joint such that movement of the second member with respect to the first member does not cause movement of the third member with respect to the second member.

23 Claims, 12 Drawing Sheets

U.S. PATENT DOCUMENTS

| | | | |
|---|---|---|---|
| 4,883,400 A | 11/1989 | Kuban et al. |
| 4,903,536 A | 2/1990 | Salisbury, Jr. et al. |
| 4,921,293 A | 5/1990 | Ruoff et al. |
| 4,967,126 A | 10/1990 | Gretz et al. |
| 5,038,089 A | 8/1991 | Szakalv |
| 5,046,375 A | 9/1991 | Salisbury, Jr. et al. |
| 5,078,140 A | 1/1992 | Kwoh |
| 5,086,401 A | 2/1992 | Glassman et al. |
| 5,105,367 A | 4/1992 | Tsuchihashi et al. |
| 5,114,300 A | 5/1992 | Shahinpoor et al. |
| 5,116,180 A | 5/1992 | Fung et al. |
| 5,193,963 A | 3/1993 | McAffee et al. |
| 5,207,114 A | 5/1993 | Salibury, Jr. et al. |
| 5,217,003 A | 6/1993 | Wilk |
| 5,238,005 A | 8/1993 | Imran |
| 5,266,875 A | 11/1993 | Slotine et al. |
| 5,299,288 A | 3/1994 | Glassman et al. |
| 5,327,790 A | 7/1994 | Levin et al. |
| 5,339,799 A | 8/1994 | Kami et al. |
| 5,350,355 A | 9/1994 | Sklar |
| 5,382,885 A | 1/1995 | Salcudean et al. |
| 5,397,323 A | 3/1995 | Taylor et al. |
| 5,430,643 A | 7/1995 | Seraji |
| 5,515,478 A | 5/1996 | Wang |
| 5,524,180 A | 6/1996 | Wang et al. |
| 5,572,999 A | 11/1996 | Funda et al. |
| 5,587,937 A | 12/1996 | Massie et al. |
| 5,618,294 A | 4/1997 | Aust et al. |
| 5,619,180 A | 4/1997 | Massimino et al. |
| 5,624,398 A | 4/1997 | Smith et al. |
| 5,625,576 A | 4/1997 | Massie et al. |
| 5,626,595 A | 5/1997 | Sklar et al. |
| 5,632,758 A | 5/1997 | Sklar |
| 5,657,429 A | 8/1997 | Wang et al. |
| 5,762,458 A | 6/1998 | Wang et al. |
| 5,792,135 A | 8/1998 | Madhani et al. |
| 5,807,377 A | 9/1998 | Madhani et al. |
| 5,808,665 A | 9/1998 | Green |
| 5,814,038 A | 9/1998 | Jensen et al. |
| 5,815,640 A | 9/1998 | Wang et al. |
| 5,855,583 A | 1/1999 | Wang et al. |
| 5,876,325 A | 3/1999 | Mizuno et al. |
| 5,878,193 A | 3/1999 | Wang et al. |
| 5,907,664 A | 5/1999 | Wang et al. |
| 5,954,692 A | 9/1999 | Smith et al. |
| 5,976,122 A | 11/1999 | Madhani et al. |
| 6,001,108 A | 12/1999 | Wang et al. |
| 6,007,550 A | 12/1999 | Wang et al. |
| 6,024,695 A | 2/2000 | Taylor et al. |
| 6,063,095 A | 5/2000 | Wang et al. |
| 6,080,181 A | 6/2000 | Jensen et al. |
| 6,120,433 A | 9/2000 | Mizuno et al. |
| 6,132,368 A | 10/2000 | Cooper |
| 6,197,017 B1 * | 3/2001 | Brock et al. | 606/1 |
| 6,223,100 B1 | 4/2001 | Green |

OTHER PUBLICATIONS

David Cassak, "R2D2 in the OR", May 1997, Start–Up, pp. 10–20.

Ikuta, et al., "Shape Memory Alloy Servo Actuator System With Electric Resistance Feedback And Application For Active Endoscope", 1988 IEEE, CH2555–1/88/0000/0427–430.

M. W. Thring, "Robots And Telechirs: Manipulators With Memory; Remote Manipulators; Machine Limbs For the Handicapped", First published in 1983 by Ellis Horwood Limited.

* cited by examiner

ARTICULATED APPARATUS FOR TELEMANIPULATOR SYSTEM

This application is a continuation application of U.S. Ser. No. 09/746,853 filed Dec. 21, 2000, which is a divisional application of U.S. Ser. No. 09/375,666 filed Aug. 17, 1999 and now U.S. Pat. No. 6,197,017, which is a continuation application of U.S. Ser. No. 09/028,550 filed Feb. 24, 1998, now abandoned.

BACKGROUND OF THE INVENTION

The invention generally relates to robotics and particularly relates to telerobotic surgery.

Telerobotic surgical devices are well suited for use in performing endoscopic (or minimal access) surgery, as opposed to conventional surgery where the patient's body cavity is open to permit the surgeon's hands access to internal organs. Endoscopic techniques involve performing an operation through small (about 5 mm to 10 mm) skin incisions through which instruments are inserted for performing the surgical procedure. A video camera may also be inserted into the patient in the area of the surgical site to view the procedure. Endoscopic surgery is typically less traumatic than conventional surgery, in part, due to the significantly reduced size of the incision. Further, hospitalization periods are shorter and recovery periods may be quicker when surgery is performed endoscopically rather than conventionally.

It is, of course, important that the surgeon have some feedback from the surgical site, e.g., visual feedback either through a camera and fiber optic cable, or through real-time computerized tomography scan imagery. Even with good visualization, however, the surgeon's tactile and position senses are physically removed from the operative site rendering the endoscopic procedure slow and clumsy. Current instrumentation, with forceps, scissors, etc., inserted into the body at the end of long slender push rods is not fully satisfactory. The use of such conventional instrumentation may result in longer operative time, and potentially higher risks, for example if a ruptured artery cannot be quickly closed off then significant blood loss may occur. Moreover, there are limitations on the type and complexity of procedures that can be performed endoscopically due, in part, to the limitations on the instruments that may be employed.

Limited development work has been undertaken to investigate the use of robots in surgery. The robot at the surgical site, however, must be small and light enough that it may be easily manipulated around and inside of the patient, yet strong enough to perform effective surgery. The controls for the robot must also be precise and not sloppy. Presently existing telerobotic systems, using manipulators both with and without haptic feedback, are generally too bulky and heavy for many endoscopic techniques, or are too weak and imprecise for surgery.

There is a need, therefore, for a micro-manipulator that is strong and precise in its movements, yet is small, light and easily manipulated.

SUMMARY OF THE INVENTION

The invention provides an articulated apparatus that includes a first link member, a second link member, and a third link member. The second link member is coupled to the first link member at a proximal end of the second link member by a first joint having a first axis of rotation. The third link member is coupled to a distal end of the second link member by a second joint. The movement of the third link member with respect to the second link member is governed by at least one tendon that passes through the first axis of rotation of the first joint such that movement of the second member with respect to the first member does not cause movement of the third member with respect to the second member.

BRIEF DESCRIPTION OF THE DRAWINGS

The following detailed description of the illustrated embodiments may be further understood with reference to the accompanying drawings in which.

The drawings are not to scale and are intended to be illustrative of the operation of various systems of the invention.

DETAILED DESCRIPTION OF THE ILLUSTRATED EMBODIMENTS

The invention provides a micro-manipulator that is suitable for use in endoscopic surgery. During use, the surgeon should have the familiarity and surety of experiencing his or her hands within the patient at the operative site, while the surgeon's hands are placed within a sensory interface outside of the patient. The sensory interface, or master robot, precisely reflects the tactile environment of the robotic hand to the operator's fingers. This haptic interface electronically connects the surgeon's hand and wrist position and motion to the micro-manipulator within the patient. The digital information communicated between the haptic interface and robotic manipulator is transmitted through the endoscopic device, whether it be a laparoscope, thoracoscope, arthroscope, laryngoscope or other minimal access surgical device.

Due to the electronic digital interface, it is not required that the haptic interface and micro-manipulator be mechanically connected. This permits civilian, as well as military, physicians to provide care to patients located in remote or potentially hostile environments via telepresence. Telepresence with appropriate sensing instruments could permit one surgeon to conduct operations at different sites (any distance apart) without traveling. Systems incorporating the invention also permit sterile isolation of the slave robot at the operation site from the master robot and surgeon.

Figure 1:
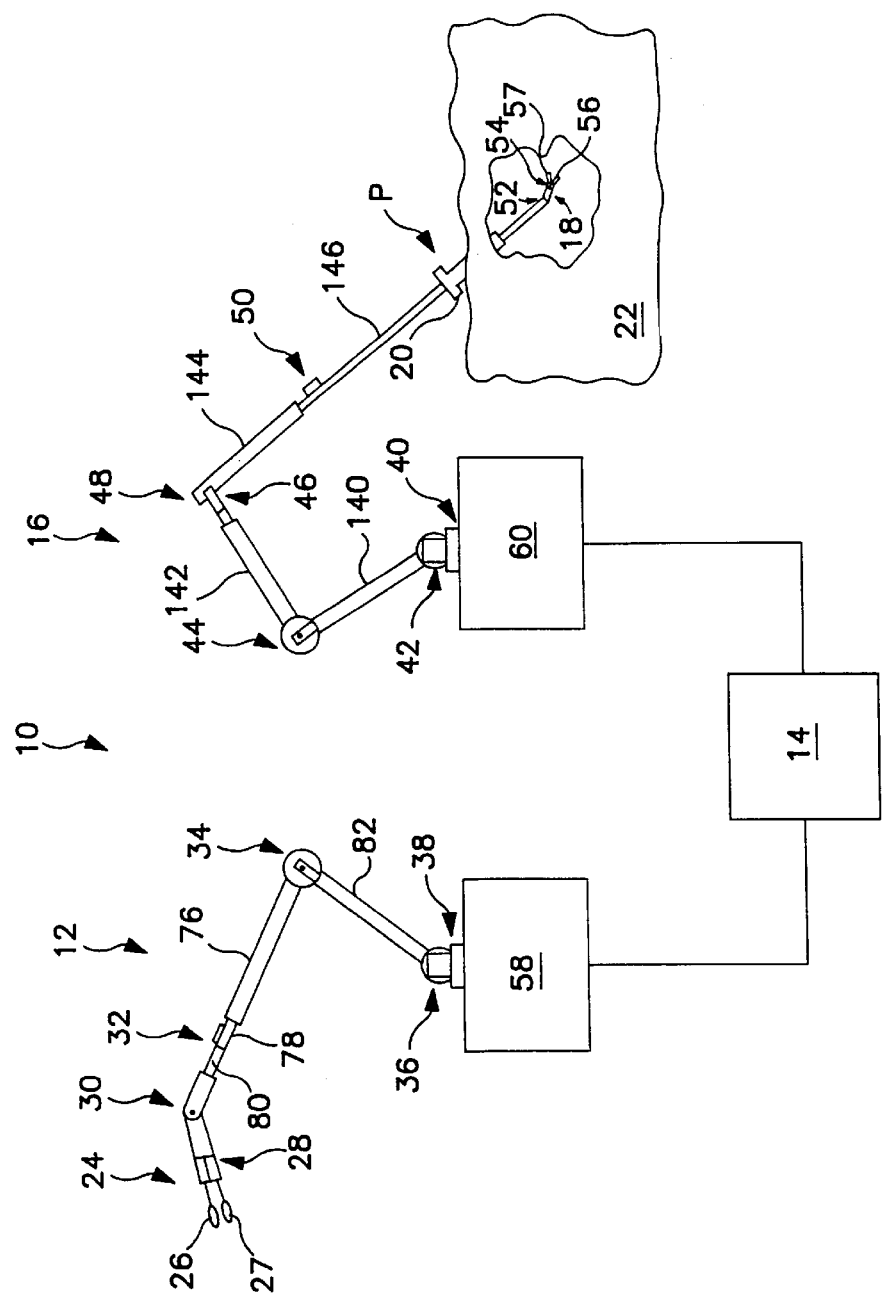
FIG. 1 shows an illustrative view of a system incorporating the benefits of the invention.

As shown in FIG. 1, a system 10 including benefits of the invention includes a master robot 12, a central processor 14, and a slave robot 16. The system may be used by positioning the end effector tip 18 of the slave robot 16 through a trocar sleeve 20 into a patient 22 during surgery. During use, a surgeon may manipulate the end effector handle unit 24 of the master robot, to effect the desired positioning and movement of the grippers on the tip unit 18 within the patient 22. The system may also include a fiber optic cable with a camera (not shown) at its distal end within the surgical site. The fiber optic cable is connected to a video system (not shown) for viewing the surgical site. The camera may be mounted on the instrument tip unit 18, or may be positioned away from the site to provide additional perspective on the surgical operation. In certain situations, it may be desirable to provide the camera through an incision other than the one through which the trocar sleeve 20 and instrument have been inserted into the patient.

The master robot 12 incudes handles 26, 27 similar to the scissor handles on a conventional surgical instrument. These handles may be independently rotated about two joints having a common axis generally indicated at 28. The pair of handles may then be rotated about a joint generally indicated at 30 that has an axis of rotation orthogonally disposed to the axis of rotation of the other two joints at 23. This structure may then be rotated axially about an axial joint generally located at 32, which in turn may be rotated about an elbow joint generally located at 34, a shoulder joint generally located at 36, and a base rotation joint generally located at 38. The relative rotational movements of these joints are diagrammatically depicted in FIG. 2.

The slave robot 16 includes a base rotation joint 40, a shoulder rotation joint 42, and an elbow rotation joint 44 each similar to the joints 38, 36, and 34 of the master robot 12. The slave robot 16 also includes two free joints 46 and 48 that provide axial and longitudinal rotation without being connected to any motors. This permits the arm of the slave robot to freely move relative the incision point through the trocar generally indicated at P. The slave robot 16 also includes an axial rotation joint 50 providing axial rotation of the tip unit 18, as well as joints 52 and 54 that provide movement of the grippers both independently and together. The relative rotational movements of these joints are also diagrammatically depicted in FIG. 2.

Significantly, the motors that control the joints proximate the handle 26 in the master robot 12 are located in the base 58, and the motors that control the joints in the slave robot 16 proximate the grippers 56, 57 are located in the base 60 of the slave robot 16. Cables extend from motors in the base up through each section and joint to control and monitor movement of the non-free joints as will be discussed further below. This permits the robots, and in particular the end effector portion of the slave robot, to be both small and light. In a preferred embodiment, all of the motors are located in the base of each respective robot.

Figure 3:
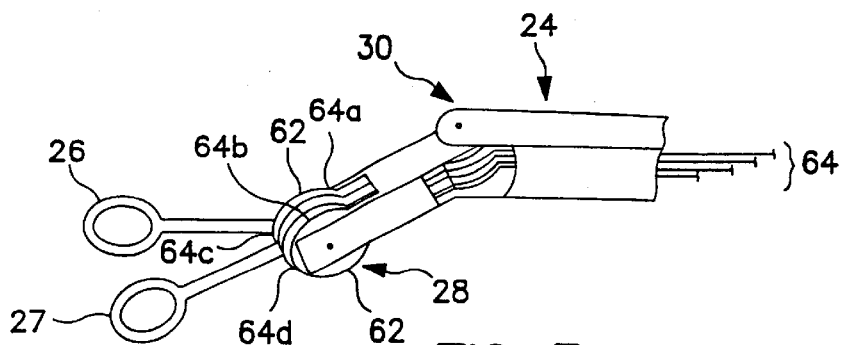
FIG. 3 shows an illustrative isometric view of the handle portion of the system of FIG. 1.
Figure 4:
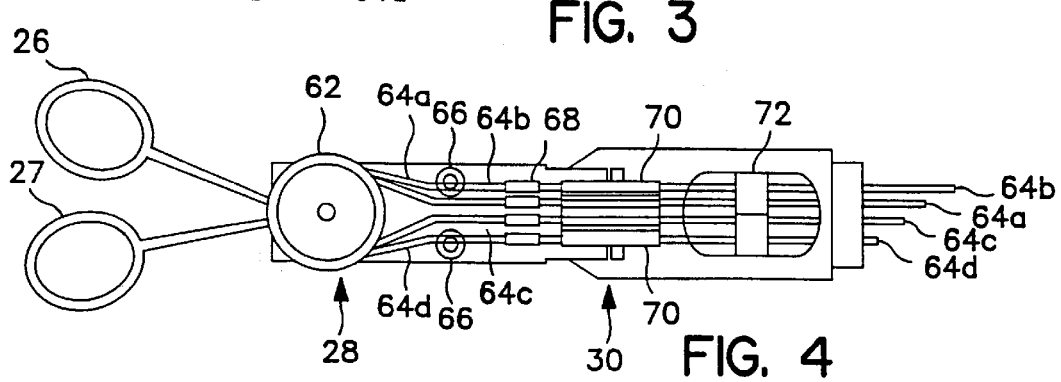
FIG. 4 shows an illustrative top view of the handle portion shown in FIG. 3 with a portion of the outer housing removed.
Figure 5:
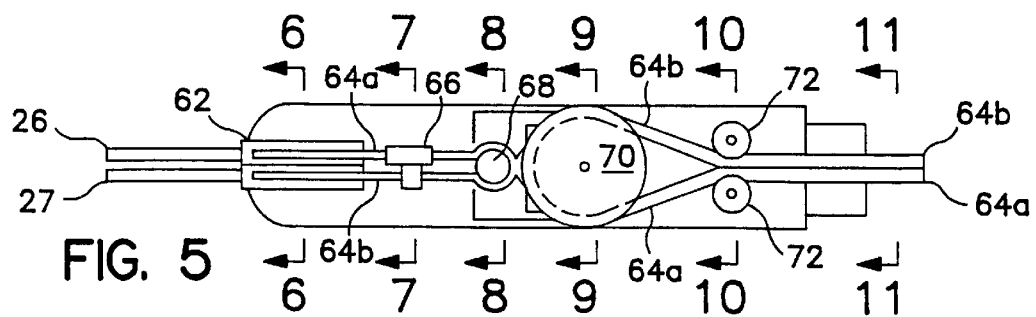
FIG. 5 shows an illustrative side view of the handle portion shown in FIG. 3 with a portion of the outer housing removed.
Figure 6:
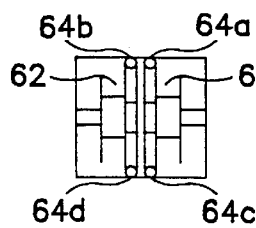
FIGS. 6 through 11 show illustrative sectional views of the handle portion shown in FIG. 5 taken along lines 6—6 through 11—11 respectively thereof.
Figure 7:
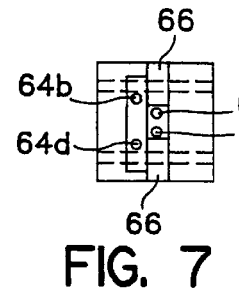
Figure 8:
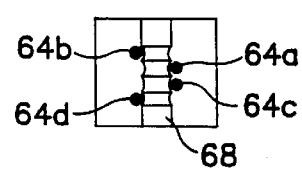
Figure 9:
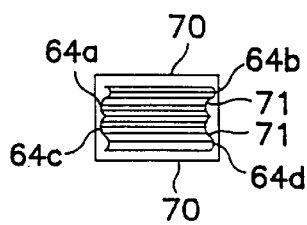
Figure 10:
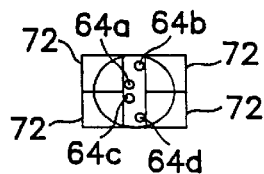
Figure 11:
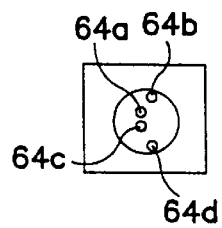

As shown in FIGS. 3 through 5, the handles 26, 27 of the system on FIG. 1 are attached to handle pulleys 62. Cables 64a–64d extend from the handle pulleys 62 and pass around additional pulleys within the handle unit 24. The cables 64 then extend toward the next proximate section of the robot, and eventually terminate in the base 58. Specifically, and with reference to the sectional views shown in FIGS. 6 through 11, the cables 64 extend from the handle pulleys 62 (FIG. 6), then pass around two split level pulleys 66 (FIG. 7), then around another pulley 68 (FIG. 8) to bring the cables near a set of four larger diameter pulleys 70 (FIG. 9), and finally to a set of four alignment pulleys 72 (FIG. 10).

The cables may be formed of any high strength, high molecular weight polyethylene (or other polymeric) fibers such as SPECTRA or VECTRAN polymers. The cables may be 80/1000 of an inch in diameter, and may be either two single loop cables that are fixed to the handle pulleys 62, or may comprise four separate cables, each of which is fixed to the handle pulleys 62. The pulleys may be formed of any suitable material, e.g., polytetrafluoroethylene (PTFE) and the guide pulleys 66, 68 and 72 may either be independently freely rotating or fixed. The various portions of pulleys 68 and 72 may also rotate independent of one another. Pulleys 62 includes two pulleys that may rotated independent of one another, and pulleys 70 include four pulleys that may rotated independent of one another. Spacers formed of PTFE tape may also be inserted between adjacent independently rotating pulleys, such as is shown between adjacent pulley wheels 70 in FIG. 9. The spacers 71 permit rotation of the pulleys relative each other with decreased friction, and help maintain placement of the cables on the pulleys.

The handle unit 24 provides three degrees of freedom of movement as follows. When one of the handles 26 is moved relative the other 27, the pairs of cables 64a and 64c will produce reciprocal movement, and the pair of cables 64b and 64d will produce reciprocal movement as may be discerned from FIG. 3. With reference to FIGS. 3, 5 and 9, however, when the handles are rotated together about joint 30 which is coincident with the centers of pulleys 70, the cables 64b and 64d will move together in a direction opposite the direction of movement of cables 64a and 64c. See FIG. 9. A surgeon, therefore, may hold the handles 26, 27 with his or her thumb and forefinger, and may place a third finger against the handle unit at the location of the housing generally indicated at A in FIG. 3. In alternative embodiments, the cables may be run in a variety of ways, for example the placement of cables 64c and 64d may be swapped on pulleys 70, 72 and 74.

Figure 12:
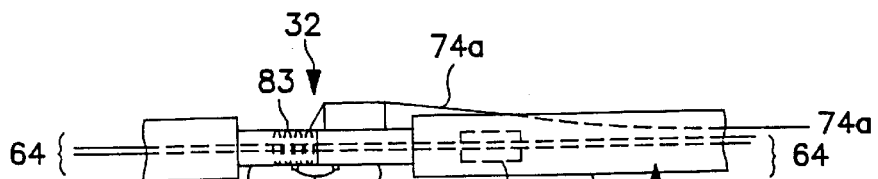
FIGS. 12 and 13 show illustrative side and top views respectively of the handle axial rotation portion of the system shown in FIG. 1.
Figure 13:
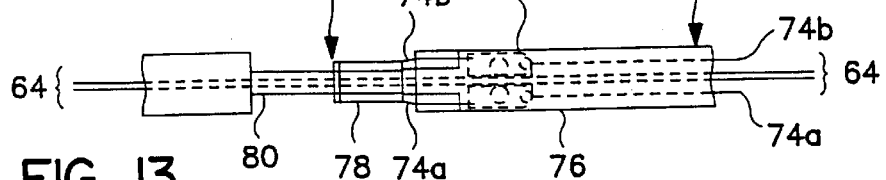
Figure 14:
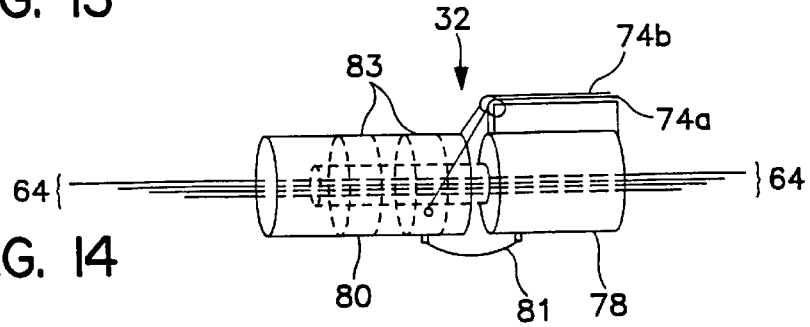
FIG. 14 shows an illustrative and partially exploded isometric view of the rotating bearings of FIGS. 12 and 13.
Figure 15:
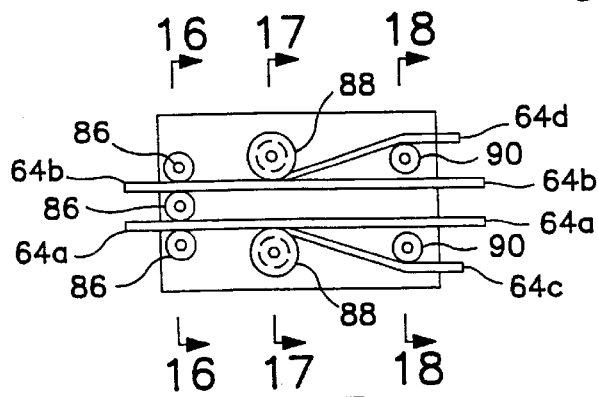
FIG. 15 shows an illustrative view of the cable collector of FIGS. 12 and 13 with its housing partially removed.

As shown in FIGS. 12 and 13, the axial rotational joint 32 on the master robot 12 of FIG. 1, is driven by two cables 74a and 74b. The cables extend radially outwardly from one robot arm member 76, around one set of pulleys each positioned over another arm member 78 fixed to the arm member 76, and then are attached to an adjoining arm member 80. By rotating the arm member 80 with respect to the arm member 76, the cables 74a and 74b will alternately move in opposite directions. A safety tie strap 82 may be fixed to each of the arms 78 and 80 to prevent rotation beyond a certain range. This will prevent damage to the cables from over rotation since the cables 64 that extend from the handle unit 24 run through the center of the arm members 78 and 80 as shown. The arm member 80 also includes internal rotational bearing 83 through which the cables pass as shown in FIG. 14. FIG. 14 illustrates the rotational relationship of the cable arms 78 and 80 (shown slightly spaced apart. The positioning of the cables 64 in the center of the sections 80 and 78 permits the section 80 to be rotated with respect to section 78 about joint 32 without significant attendant movement of the cables 64.

Figure 16:
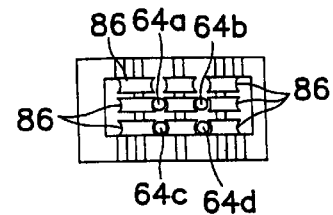
FIGS. 16 through 18 show illustrative sectional views of the cable collector of FIG. 15 taken along lines 16—16 through 18—18 respectively thereof.
Figure 17:
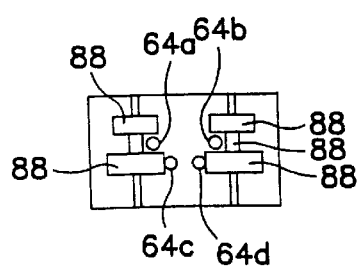
Figure 18:
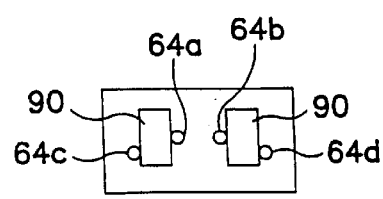
Figure 19:
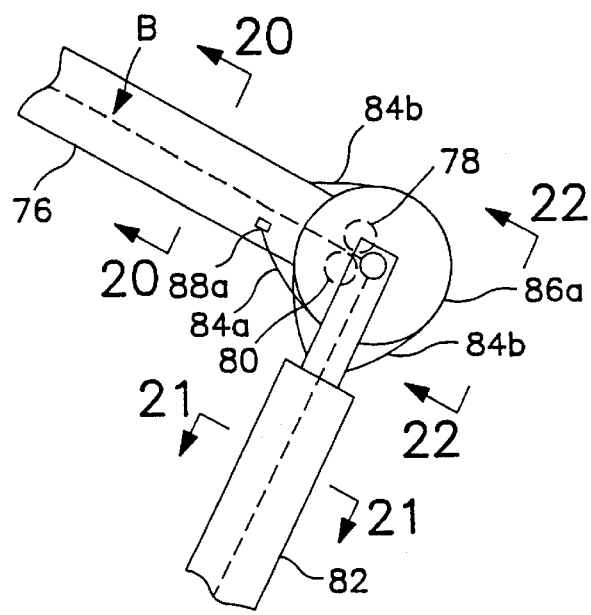
FIG. 19 shows an illustrative side view of the elbow joint portion of the master robot shown in FIG. 1.

As shown in phantom in FIG. 12, a cable collector 84 is located within the robot section 76. The cable collector 84 receives the cables 64 that are positioned within the center of the sections 80 and 78, and distributes the cables approximately along a plane B that is extends within the section 76 toward the next joint as shown in FIGS. 12, 13 and 19. Cable collectors similar to cable collector 84 are used in several other places in the robots 12 and 16, wherever it is convenient to receive a centrally bundled set of cables at one end and produce a planar distribution of the cables at the other end, or vice versa. The cable collector 84 may be used to distribute six cables instead of the four shown by feeding the two additional cables through the upper pulleys 86 shown in FIG. 16 (similar to cable pairs 64a, 64b and 64c, 64d). The fifth and sixth cables would then pass around the upper pulleys 88 shown in FIG. 17 (similar to cables 64c, 64d), and finally around the outside of the pulleys 90 (again, similar to the cables 64c and 64d). Applicants have discovered that although the two additional cables will be positioned directly above the two other cables (64c and 64d), the two upper cables will fan out away from the cables 64a–64d to form the planar distribution, in part, because the receiving pulleys at the elbow joint 34 urge the cables to form a planar distribution.

Figure 20:
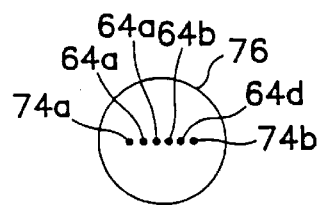
FIGS. 20 and 21 show illustrative sectional views of the elbow joint portion shown in FIG. 19 taken along lines 20—20 and 21—21 thereof.
Figure 21:
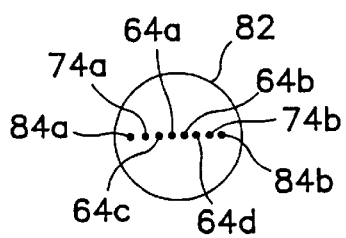
Figure 22:
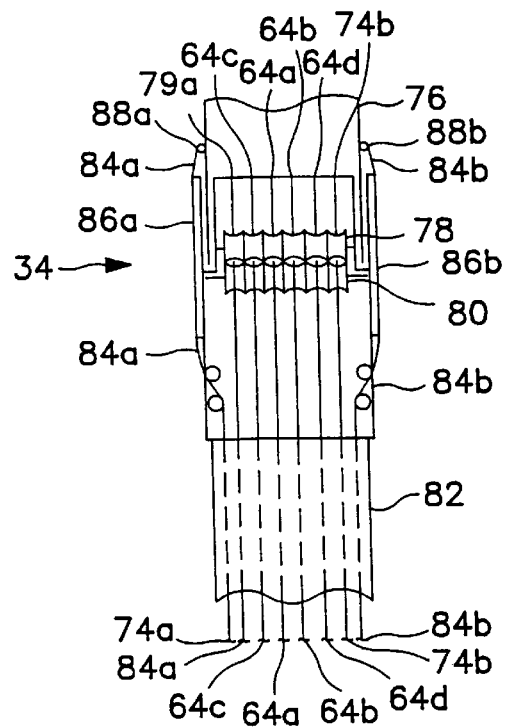
FIG. 22 shows an illustrative rear view of the elbow joint of FIG. 19 taken along line 22—22 thereof.

The cables 74a and 74b that control the axial rotation joint 32 extend above the cable connector 84 within the section 84, and approach the plane B, as shown in FIGS. 19 and 20. The cables 64 and 74 are received between two sets of pulleys 78 and 80, each set including six mutually independently rotatable pulleys as shown in FIG. 22. The pulleys 78 and 80 ensure that the cables 64 and 74 remain approximately in the center of the joint 34 as the section 80 is rotated about the section 78 of the robot 12. This permits the section 76 to be rotated with respect to the section 82 about the joint 34 without significant attendant movement of the cables 64 and 74.

The joint 34 is actuated by either of cables 84a and 84b which extend around pulleys 86a and 86b respectively in opposite directions, and terminate at fixed points 88a and 88b respectively on opposite sides of section 76 as shown in FIGS. 19 and 22. The cables 64, 74, and 84 extend through the section 82 along a plane generally indicated at C in FIG. 22.

Figure 23:
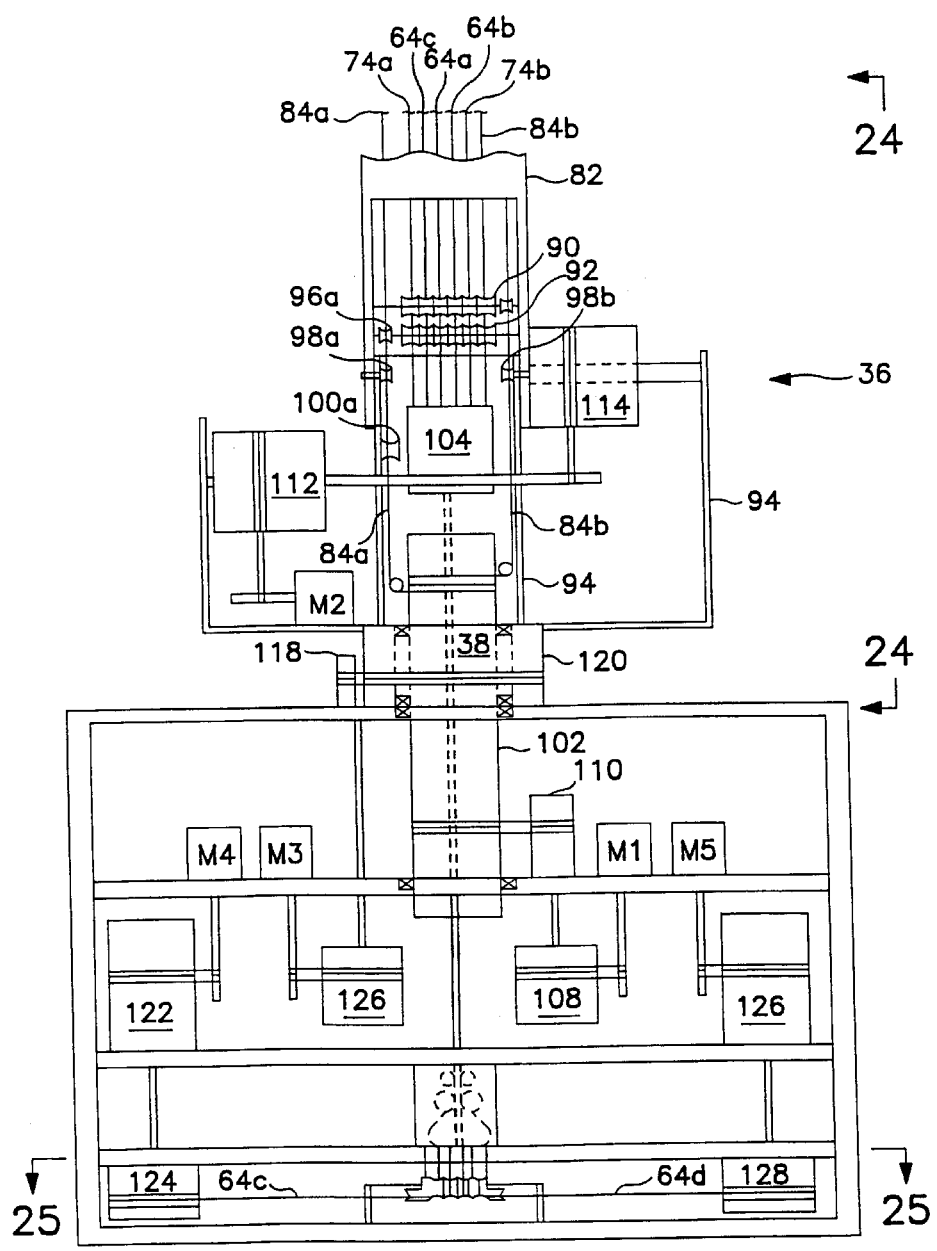
FIG. 23 is an illustrative front view the base and shoulder portions of the master robot of FIG. 1.
Figure 24:
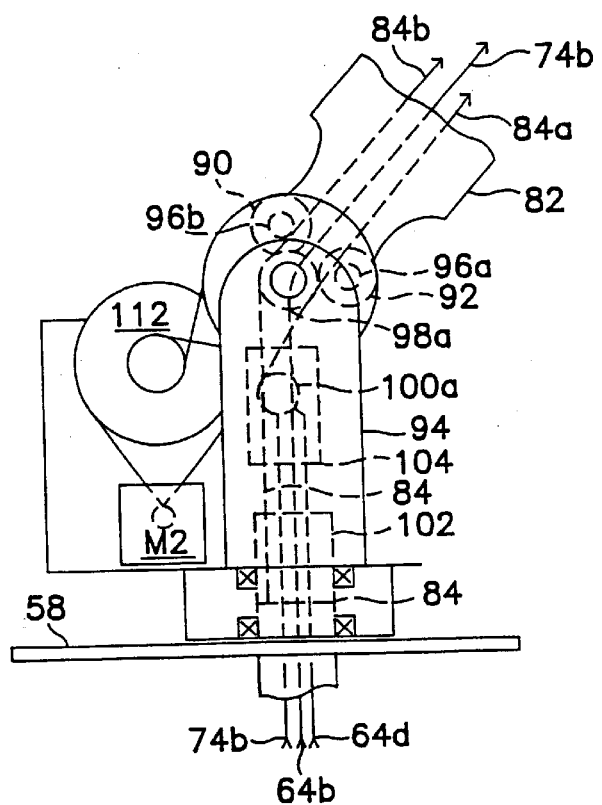
FIG. 24 is an illustrative side view of the shoulder portion of the robot of FIG. 1 taken along line 24—24 of FIG. 23.

As shown in FIG. 23, the cables 64, and 74 are received between another two sets of pulleys 90 and 92 at the proximal end of section 82 within joint 36. Each set of pulleys 90 and 92 also includes six independently rotatable pulleys, and the pulleys 90 and 92 are positioned to permit the cables 64 and 74 to extend through approximately the center to the joint 36. The section 82 may therefore be rotated with respect to the base section 94 about joint 36 without significant attendant movement of the cables 64 and 74. The cables 84a and 84b extend through the joint 36 around pulleys 96a and 96b respectively, and then around pulleys 98a and 98b respectively as shown in FIGS. 23 and 24. The cable 84a then wraps around one more pulley 100a, and then both cables 84a and 84b are brought to a hollow termination cylinder 102. In a preferred embodiment, the ends of the two cables 84 wrapped around the cylinder 102 are attached to each other, forming a single cable 84. As the cylinder 102 is rotated between alternate directions, the joint 34 is actuated in mutually opposing directions.

Figure 2:
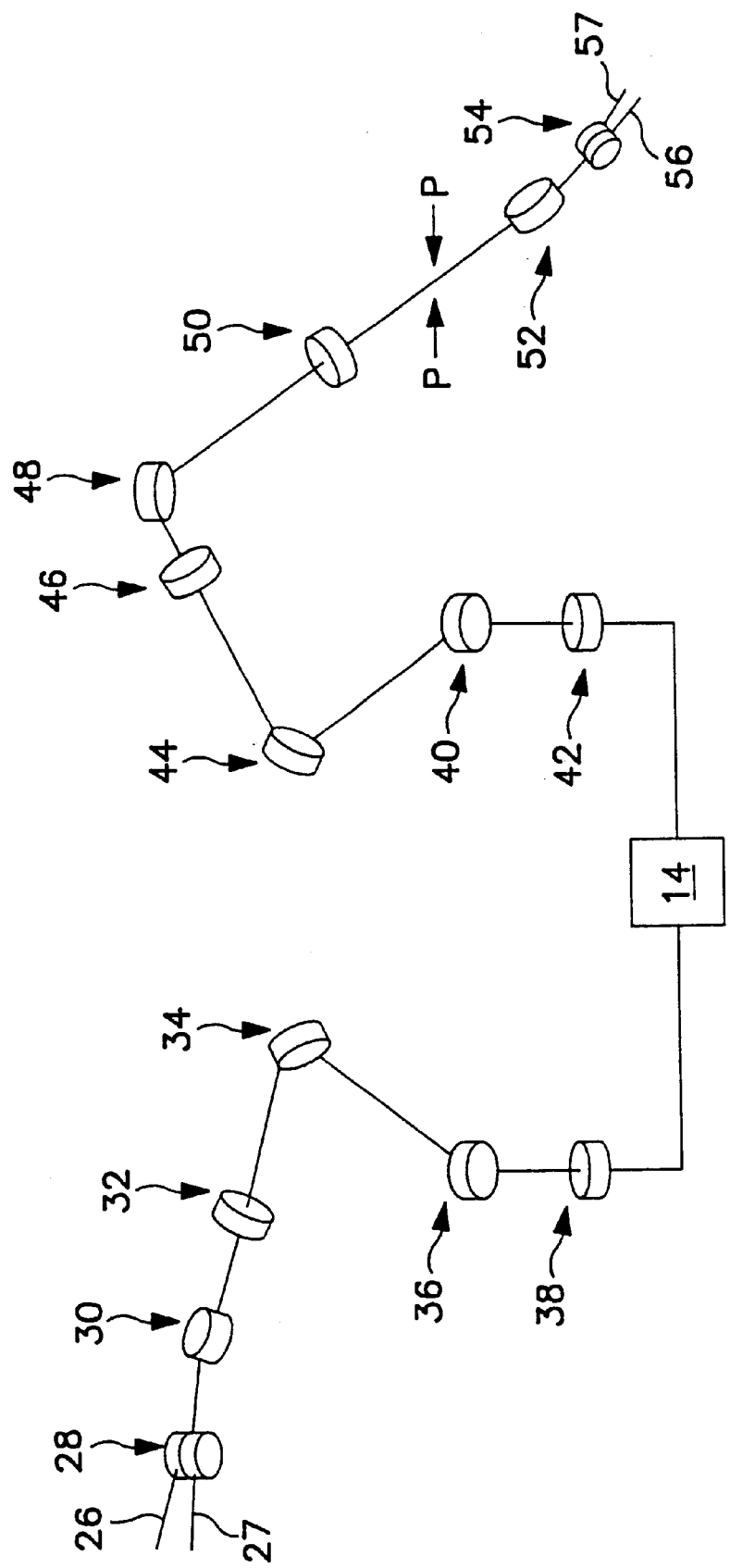
FIG. 2 shows a diagrammatic representation of the relative rotational movements of the joints in the system of FIG. 1.

The shoulder section 94 may be rotated with respect to the base 106 providing a joint 38 that has an axis of rotation that is perpendicular to the axis of rotation of the joint 36 (as shown in FIG. 2). The cables 64 and 74 extend through a cable collector 104 similar to the cable collector described above with reference to FIGS. 15–18, except that six cables are run through the cable collector 104. The cables extend from the collector 104 toward the base 106 in three pairs that are positioned such that cables 74a and 74b are visible in FIG. 23, and cables 74b, 64b, and 64d are visible in FIG. 24.

Rotation about joint 34 may be effected by controlling the movement of the motor M1, which causes cylinders 108, 110 and 102 to rotate, thereby effecting movement of cables 84 causing rotation of the section 76 with respect to section 82 with respect to the joint 34.

Rotation may be effected about joint 36 by controlling the movement of the motor M2, which causes cylinders 112 and 114 to rotate. Cylinder 114 is fixed to the section 82, so rotation of the cylinder 114 causes rotation of the section 82 with respect to the shoulder section 94 about joint 36.

Rotation about joint 38 may be achieved by controlling the movement of the motor M3, which causes cylinders 116, 118, and 120 to rotate, thereby effecting movement of the shoulder section 94 with respect to the base 106 about joint 38.

Figure 25:
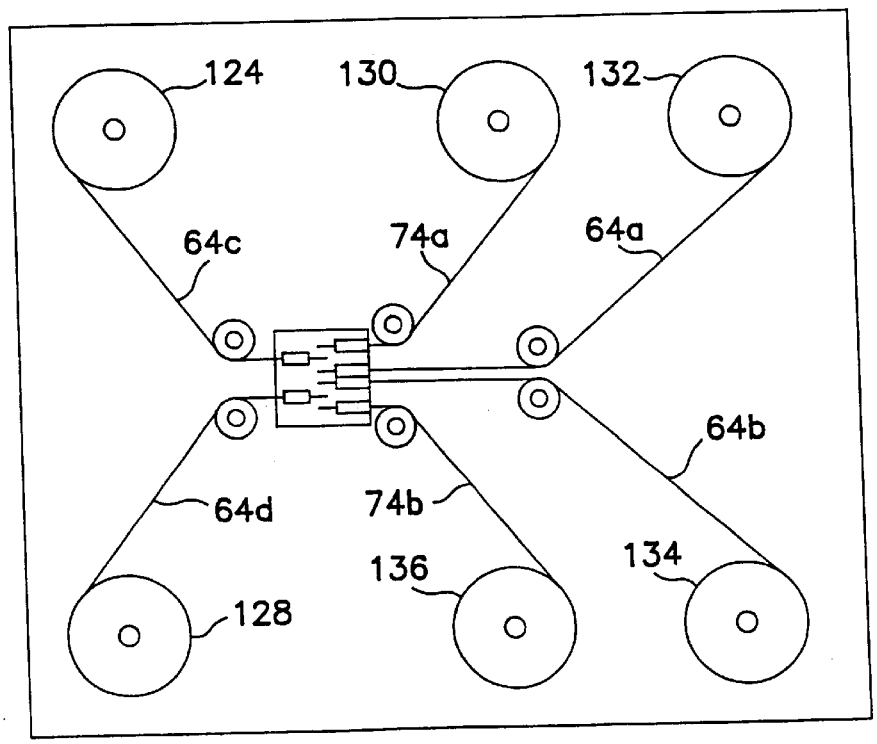
FIG. 25 is a plan view of a portion of the base portion of FIG. 23 taken along line 25—25 thereof.
Figure 26:
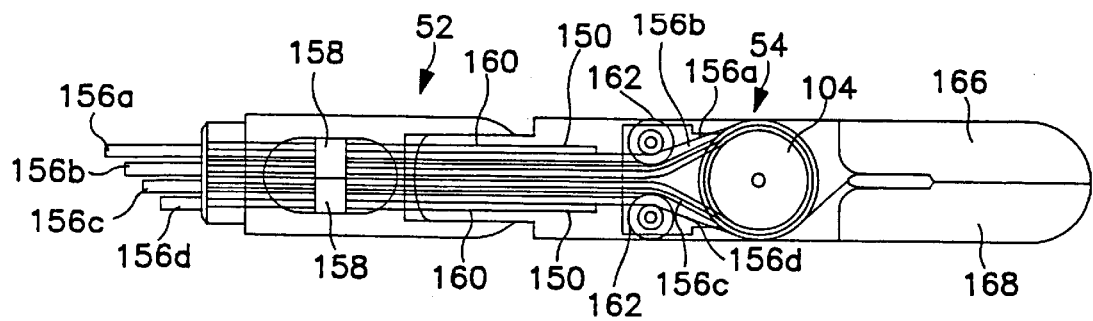
FIGS. 26 and 27 are illustrative top and side views respectively of the gripper portion of the system of FIG. 1 with the housing partially removed.

The remaining six joints are controlled by the remaining six motors in the base. Only two of the remaining motors M4 and M5 are shown in FIG. 23. The other four motors are positioned in the base behind the drive system for motors M4 and M5, as indicated in FIG. 25, and operate similar to the systems of motors M4 and M5. In particular, cable 64c may be drawn toward the base by controlling the movement of the motor M4, which causes cylinders 122 and 124 to rotate. Similarly, cable 64d may be drawn toward the base by controlling the movement of the motor M5, which causes cylinders 126 and 128 to rotate. With reference to FIGS. 23 and 25, it can be seen that the other cables 64a, 64b, 74a and 74b may be similarly controlled by four other motors and associated cylinders, including cylinders 130, 132, 134 and 136 as shown.

The gearing ratios of the base rotation joint 38 (associated with M3), the shoulder joint 36 (associated with M2) and the elbow joint 34 (associated with M1) should each be about 40 to 1, while the gearing ratios of the remaining joints should be about 8 to 1.

The slave robot 16 is identical to the master robot from the base up to the joint 46, with the one exception that the gearing ratio for the remaining joints (that was 8 to 1 with the master) is 20 to 1 for the slave robot 16. Specifically, the joint 40 on the slave robot 16 is similar to the joint 38 on the master robot 12, and the joint 42 on the slave robot is similar to the joint 36 on the master robot, and the joint 44 on the slave robot is similar to the joint 34 on the master robot. The slave robot also includes cable tracking through the base 60 and shoulder section and section 140 similar to the cable tracking of the master robot 12 through the base 58, shoulder section 94 and section 82.

In the slave robot 16, the joints 46 and 48 are not controlled by any motors. The joint 46 is similar to the joint 32 described above with reference to FIGS. 12 through 18 except that there are no cables that extend radially outwardly from the section 142 similar to the cables 74 that extend out from the section 76 on the master robot 12. There are six cables that extend through the section 142. The cables are collected by a cable collector (as discussed above) prior to the joint 46 where they are redistributed from a planar arrangement to a centrally positioned collection. The six cables then pass through the joint 46 centrally positioned similar to that shown in FIG. 14. Following the joint 46, the cables are again redistributed by another cable collector from the central position to a planar distribution.

The six planar distributed cables are then fed between two sets of pulleys at the joint 48 as described above with reference to FIGS. 19–22, except that all of the cables pass through the joint. There are no pulleys at joint 48 similar to the pulleys 86 at joint 34. Joints 46 and 48 are passive joints.

The six cables then continue through the subsequent section 144. The joint 50 is identical to (though smaller in scale than) the joint 32, and is driven by two cables in the same fashion that cables 74a and 74b drive joint 32 as discussed above with reference to FIGS. 12–18. A cable collector is also positioned on the proximate side of the joint 50 to redistribute the remaining four cables into the center of the section 146. The section 146 (together with the remaining four cables) pass into a patient 22 through the trocar sleeve 20.

Figure 27:
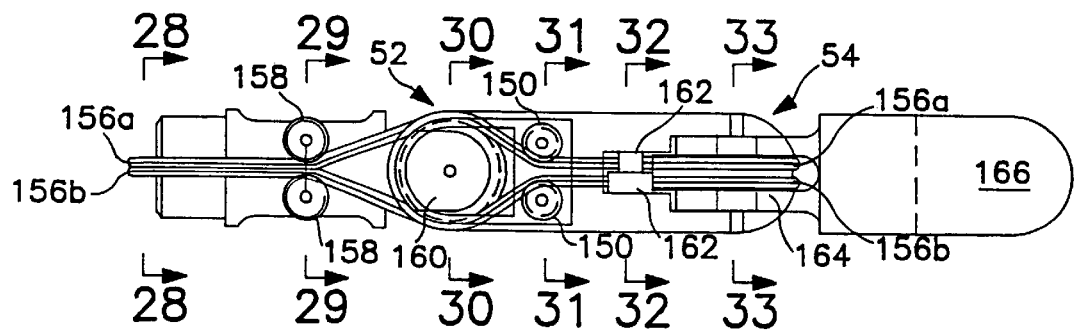
Figure 28:
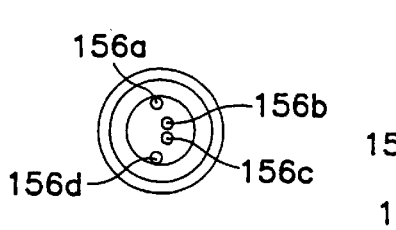
FIGS. 28–33 are illustrative sectional views of the gripper portion of FIG. 27 taken along lines 28—28 through 33—33 respectively thereof.
Figure 29:
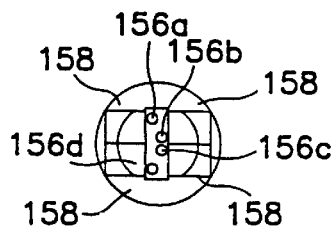
Figure 30:
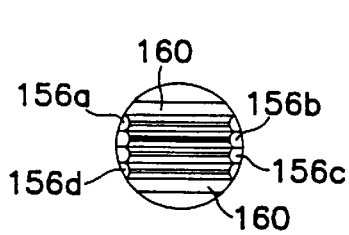
Figure 31:
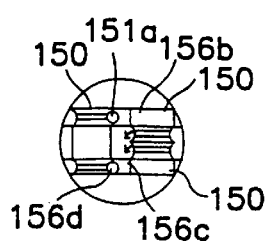
Figure 32:
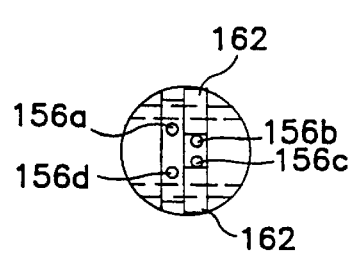
Figure 33:
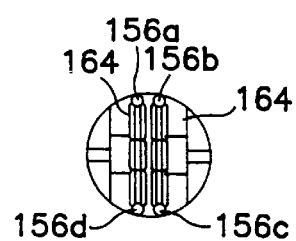

As shown in FIGS. 26–33, the gripper portion 18 is similar to (though smaller in scale than) the handle portion 24, except that where the handle portion included a single pulley wheel (pulley 68 in FIGS. 5 and 8), the associated arrangement of the gripper portion includes two pulley wheels (see pulleys 150 of FIGS. 27 and 31). Generally, cables 156a–156d extend through the gripper portion around pulleys 158 (FIG. 29), around pulleys 160 (FIG. 30), around pulleys 150 (FIG. 31), around pulleys 162 (FIG. 32), and terminate on pulleys 164 (FIG. 33) as shown.

The cables 156 may be formed as discussed above in connection with the handle portions shown in FIGS. 3–11, and the guide pulleys 150, 158, and 162 may be independently freely rotating or fixed. Again, PTFE spacers may be placed between adjacent, independently rotating pulleys.

The gripper unit provides three degrees of freedom as follows. When one of the cables, 156a, is moved relative the other of its air, 156d, the associated gripper 166 will rotate with respect to the central axis of the pulley 164. Similarly, when one of the cables 156b is moved relative the other of its pair, 156c, then the associated gripper 168 will rotate with respect to the central axis of the pulley 164. When both of cables 156a and 156d are pulled with respect to the other cables 156b and 156c (and vice versa), then the gripper unit will rotate with respect to the central axis of the pulleys 160. See FIGS. 27 and 30.

Figure 34:
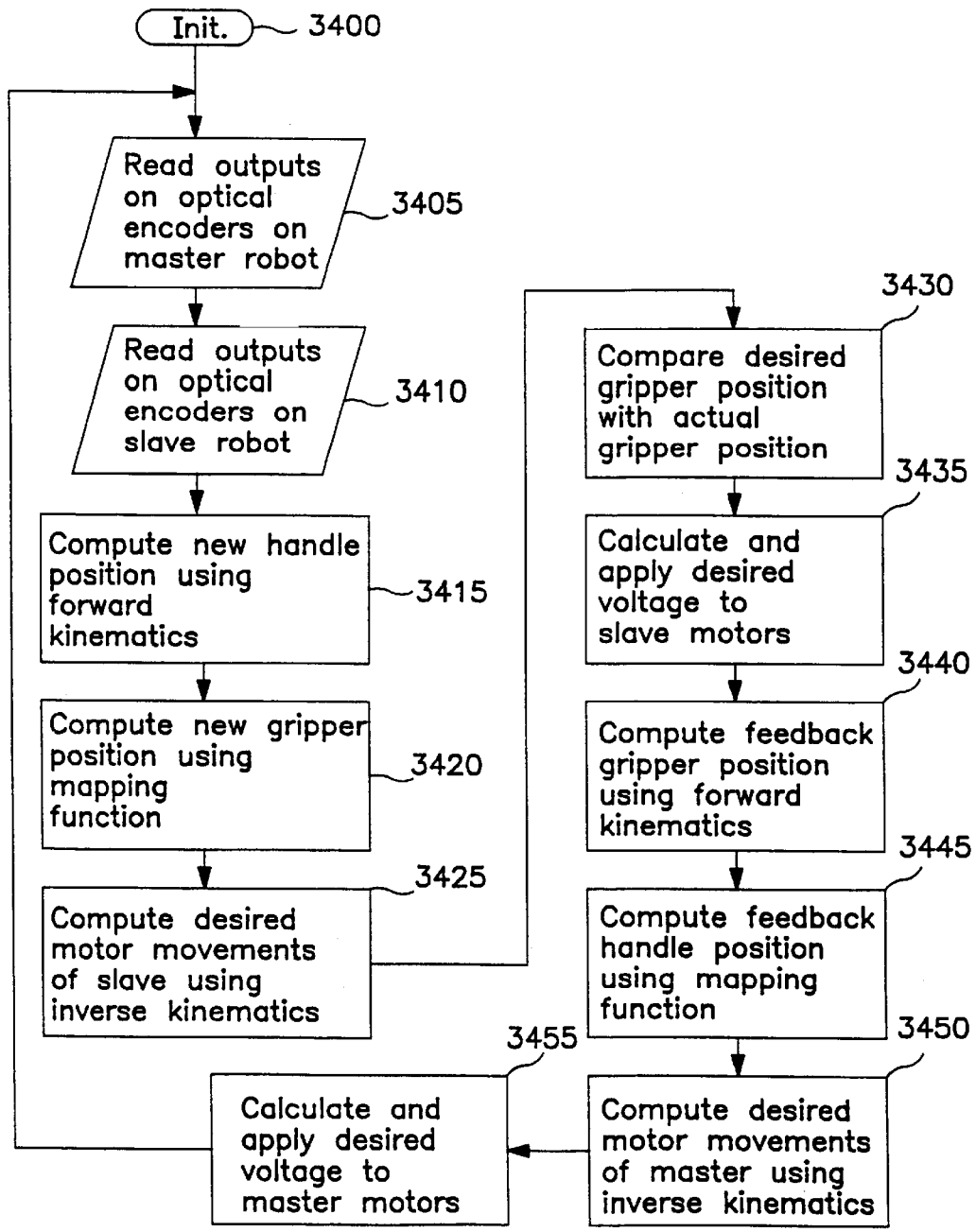
FIGS. 34 and 35 show operational steps of different embodiments of systems incorporating the invention.

During operation, and with reference to the flow chart shown in FIG. 34, a system including robotic manipulators of the invention, begins (step 3400) by initializing variables and establishing a home position for the master and robot slaves. The system (step 3405) then reads the outputs of the optical encoders to identify movement of the joints of the master robot. The system also reads the outputs of the optical encoders of the slave robot (step 3410) for identifying feedback. The feedback information is utilized later in the process loop. The system then computes the new position of the handle based on the position sensor signals read from the optical encoders of the master robot (step 3415). A new gripper position is then computed (step 3420) based on the new handle position and a predetermined mapping function that maps handle position to gripper position. The desired motor movements of the slave robot (step 3425) are then computed based on the new desired position of the gripper using inverse kinematics. The desired gripper position is then compared (step 3430) with the actual gripper position as known from monitoring the optical encoder outputs of the slave robot motors. The voltages required to move the gripper to the desired position are then calculated and applied (step 3435) proportional to the difference between the desired and actual positions of the gripper.

A feedback gripper position is then computed (step 3440) based on the outputs of the optical encoders of the slave robot, using forward kinematics. The associated handle position is then computed (step 3445) based on the feedback gripper position using the mapping function, and the desired motor movements are calculated for the master robot using inverse kinematics (step 3450). The feedback voltages are applied to the required motors of the master robot (step 3455) to effect the required feedback from the slave robot. The process then returns to step 3405 and begins again. The system may cycle very rapidly, providing continuous actuation and feedback responses. The forward and inverse kinematical equations are well known in the art, as is the generation and use of three space mapping functions.

Figure 35:
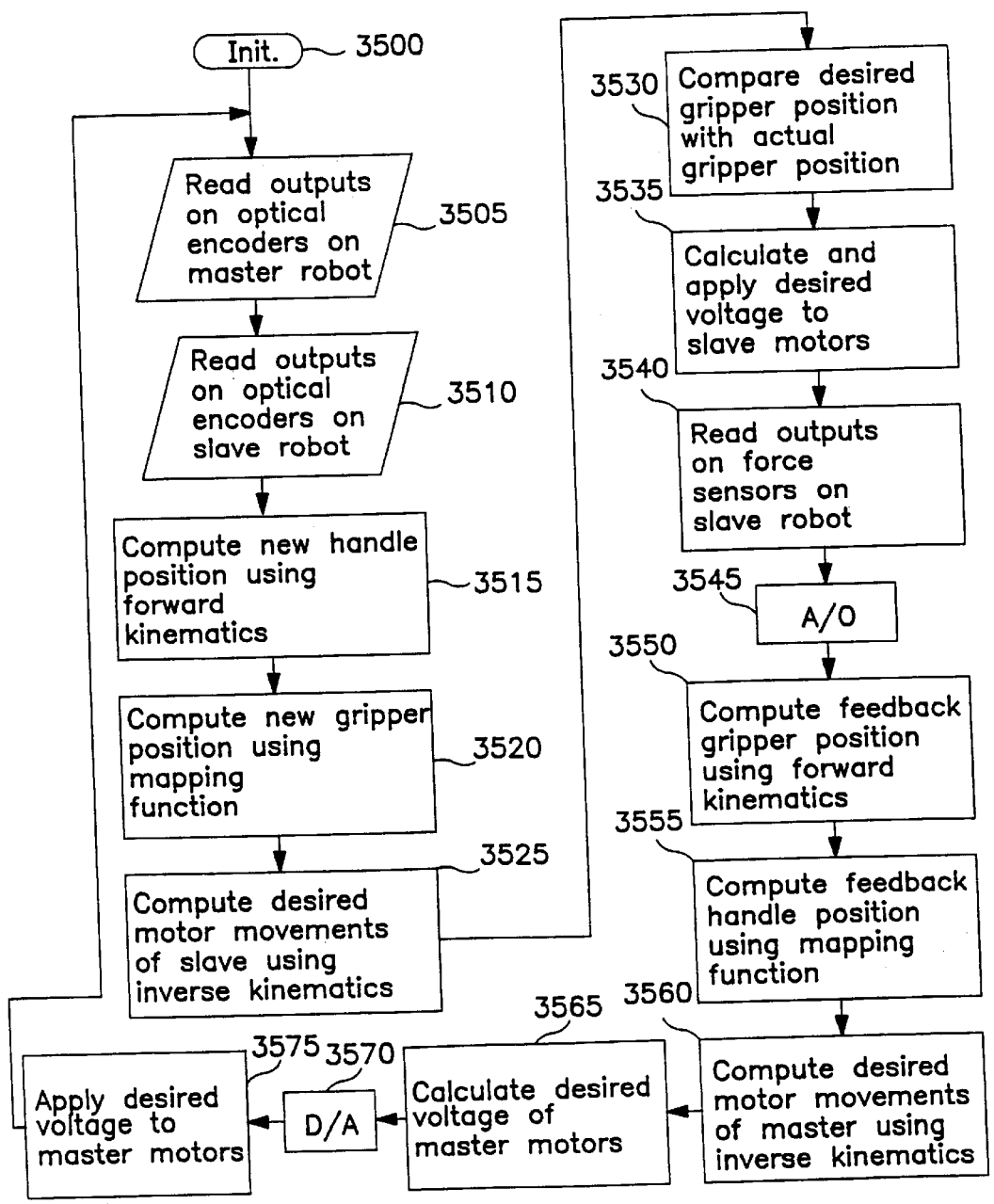

The process of FIG. 35 is similar to the process of FIG. 34 except that the feedback signals are responsive to torque sensors instead of position sensors. Steps 3500–3535 are the same as steps 3400–3435 of FIG. 34. The system of FIG. 35 then reads the outputs from torque force sensors on the slave robot (step 3540), which outputs are then digitized (step 3545). A set of feedback gripper forces are then calculated based on the torque sensor outputs using forward kinematics (step 3550). Feedback handle forces are then computed from the feedback gripper forces by using a mapping function (step 3555), and the desired motor movements of the master robot may then be calculated by inverse kinematics (step 3560). The required voltages to be applied to the master robot motors may then be calculated (step 3565), converted to analog signals (step 3570), and then applied to the master robot motors (step 3575) to effect the required feedback onto the master robot. The process then returns to step 3505 and begins again.

Figure 36:
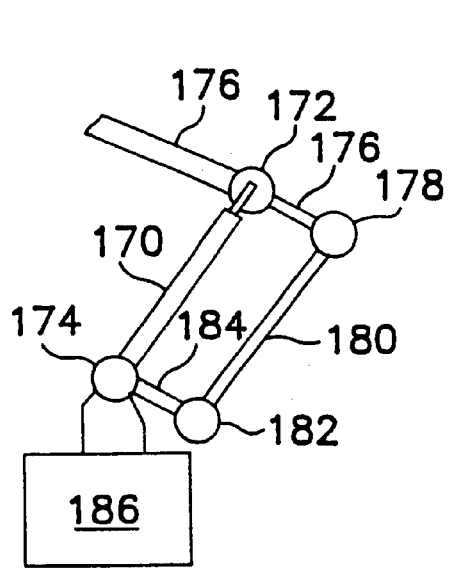
FIGS. 36 and 37 show illustrative side views of a portion of another embodiment of the invention involving a four bar linkage in two different positions.
Figure 37:
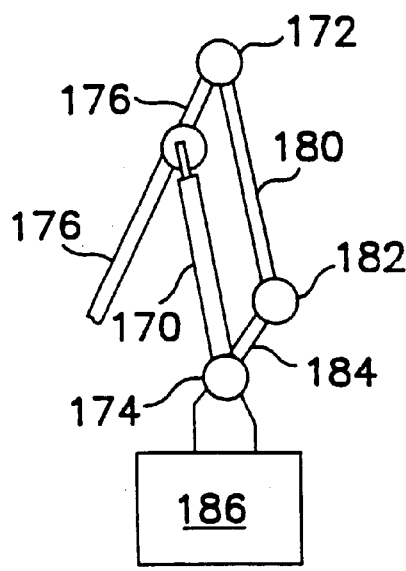

As shown in FIGS. 36 and 37, in an alternative embodiment of a system incorporating the benefits of the invention, a robot may include a four bar linkage system. Specifically, the link 170 is analogous to the link 82 of the system shown in FIG. 1, and the joints 172 and 174 are analogous to the joints 34 and 36 of FIG. 1. The cables controlling the link members at the distal end of the robot may run through the joints 174 and 172 as well as the member 170 similar to the system of FIG. 1.

In the system of FIGS. 36 and 37, however, the link 176 (which is analogous to the link 76 of FIG. 1), extends beyond the joint 172. The extended portion of member 176 is connected to another joint 178, which in turn connects to member 180. Member 180 is connected at joint 182 to member 184 which extends to joint 174. Members 176 and 184 are always parallel to each another, as are members 170 and 180 always parallel to each other. The joint 172 is actuated in the present embodiment, by having a cable extend from the base 186 around a pulley at the joint 174 and fasten to member 184. When this cable is pulled, the member 184 rotates with respect to the joint 174, rotating the member 176 with respect to the joint 172. The four bar linkage system, therefore, replaces the elbow joint 34 actuator system of FIG. 1. The system of FIGS. 36 and 37 permits the elbow joint to be actuated from closer to the base, and may provide for greater strength and rigidity.

Figure 38:
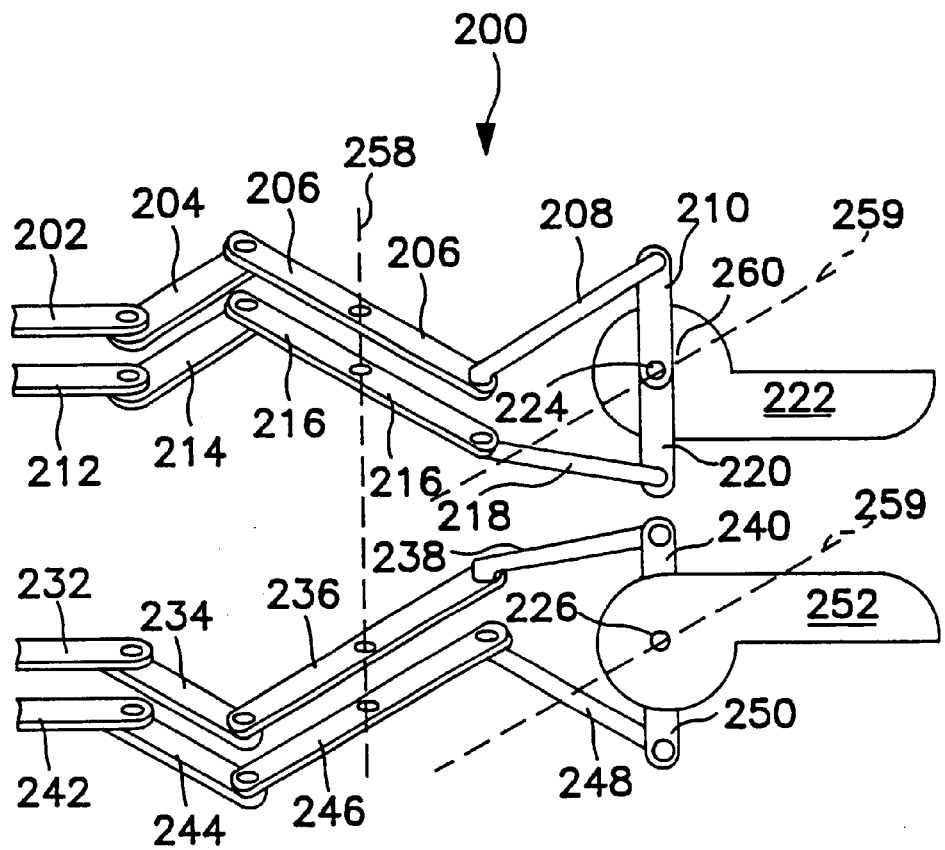
FIG. 38 shows an illustrative isometric view of another embodiment of a gripper mechanism of a system of the invention.

As shown in FIG. 38, an alternative embodiment of a gripper unit 200 of the invention includes link members instead of the cables and pulleys of FIGS. 26–33. Specifically, one half of the gripper unit 200 includes links 202–220 for controlling gripper 222, and the other half of the gripper unit includes links 232–248 for controlling gripper 252. The gripper unit halves are shown in somewhat exploded view. The grippers 222 and 252 should be adjacent one another during operation such that they may each rotate about their respective openings 224 and 226 that are mounted along a common axis 259 that is shown in exploded view in FIG. 38. The face of gripper 222 that does not include the links 210 and 220, is adjacent the face of gripper 252 that does not include the links 240 and 250.

Each of link members 206, 216, 236 and 246 include openings 228, 230, 254 and 256 respectively, that mutually align along an axis generally indicated at 258. In various embodiments, the links 206, 216, 236 and 246 may be stacked in different orders along the axis 258. For example, the links may be ordered from top down as 206, 216, 236 and 246, or they may be interleaved as 206, 236, 216 and 246.

Figure 39:
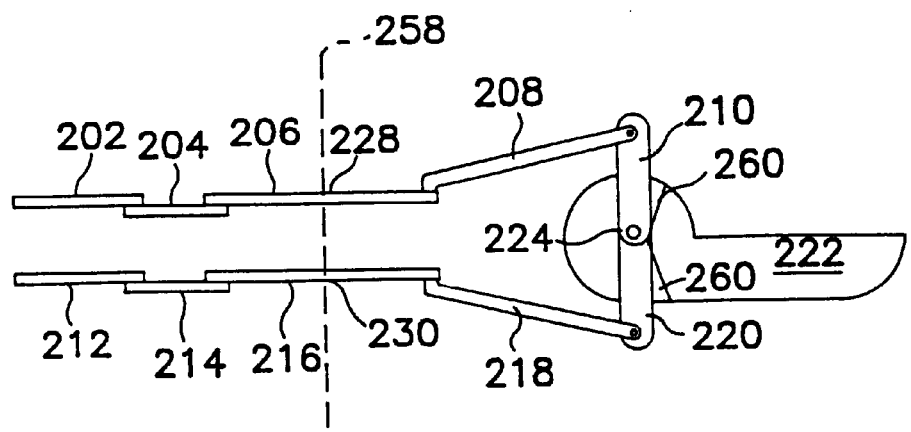
FIG. 39 shows an illustrative side view of a portion of the gripper assembly shown in FIG. 38.
Figure 40:
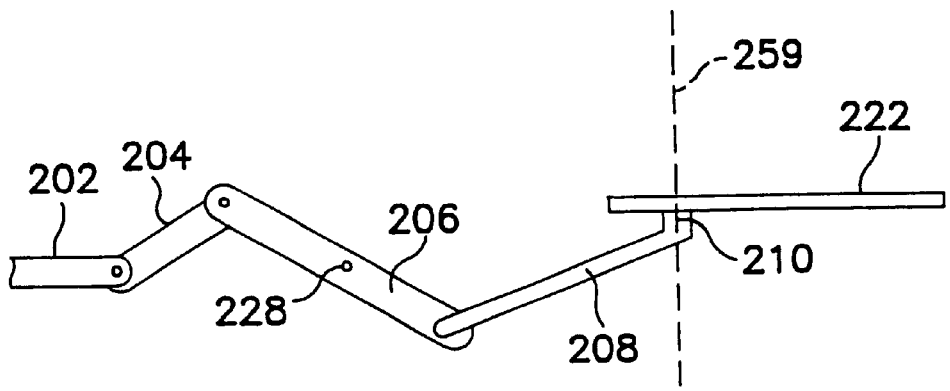
FIG. 40 shows an illustrative top view of the portion of the gripper assembly shown in FIG. 39.

As shown in FIG. 39, in a side view of one half of the gripper unit 200 of FIG. 38, it can be seen that adjacent links rotate about joint axes that are parallel with the axis 258. As shown in FIG. 40, the gripper 222 rotates about the axis 259 through opening 224 that is orthogonal to the axis 258. The links 206, 216, 236 and 246 may rotate about the axis 258, but are otherwise fixed in place. The grippers 222 and 252 may rotate about the axis 259, and the secured a fixed distance from the axis 258, but the pair of grippers 222 and 252 are together rotatable with respect to the axis 258.

During use, when link 202 is pulled away from the axis 258 with respect to link 212, then link 210 will rotate (clockwise in FIG. 39) until it contacts a stop 260 on the gripper 222. When the stop 260 is contacted and link 202 continues to be pulled away from the axis 258, then gripper 222 will begin to rotate (clockwise in FIG. 39) about its opening 224. Pulling link 212 away from the axis 258 may similarly cause the gripper 222 to rotate (counterclockwise in FIG. 39) about the opening 224 when link 220 contacts stop 262 on the gripper 222. The second portion of the gripper unit including gripper 252 may be caused to rotate in a similar fashion by pulling links 232 or 242 away from the axis 258.

If link members 202 and 212 are both pulled away from the axis 258, then the entire gripper assembly (including grippers 222 and 252) will rotate (counterclockwise in FIG. 40) about the axis 258. Similarly, if links 232 and 242 are both pulled away from the axis 258, then the entire gripper assembly will rotate (clockwise in FIG. 40) about the axis 258.

The gripper assembly 200 may provide greater strength, and reduced size. Moreover, the gripper assembly 200 may also provide improved access through extremely small openings. If the links 210 and 220 are rotated about the axis 259 such that the outer ends of the links 210 and 220 are drawn toward the axis 258 and close to one another, and the links 240 and 250 of the gripper 252 are similarly collapsed upon one another, then the gripper assembly 200 may be introduced through an opening that is only the size of the round portion of the grippers 220 and 252. Once introduced through the small opening, the links 210, 220, 240 and 250 may be rotated outward to their respective stops (e.g., 260 on gripper 222), whereupon the gripper assembly 200 may be employed within a patient.

Any of the various features of the invention disclosed herein may be employed in a wide variety of systems. Those skilled in the art will appreciate that modifications and variations may be made to the above disclosed embodiments without departing from the spirit and scope of the invention.

What is claimed is:

1. An articulated apparatus comprising:
   a first link member;
   a second link member coupled to said first link member at a proximal end of said second link member by a first joint having a first axis of rotation; and
   a third link member coupled to a distal end of said second link member by a second joint, the movement of said third link member with respect to said second link member being governed by at least one tendon that passes through said first axis of rotation of said first joint such that movement of said second link member with respect to said first link member does not cause movement of said third link member with respect to said second link member.

2. An articulated apparatus as claimed in claim 1, wherein said apparatus further includes a base portion including drive means for controlling the movement of each said link member with respect to other link members.

3. An articulated apparatus as claimed in claim 1, wherein said at least one tendon includes a cable having a diameter of about 80/1000 inch.

4. An articulated apparatus as claimed in claim 1, wherein at least one of said first, second and third link members may be inserted into a patient during endoscopic surgery.

5. An articulated apparatus comprising:
   a first link member;
   a second link member coupled to said first link member at a proximal end of said second link member by a first joint having a first axis of rotation; and
   at least one tendon extending through said first axis of rotation of said first joint such that movement of said second link member with respect to said first link member is independent of movement of said at least one tendon with respect to said first joint, said tendon being movable in a tendon direction that is transverse to the first axis of rotation to effect movement of a third link member with respect to said second link member.

6. An articulated apparatus as claimed in claim 5, wherein said apparatus further includes a second tendon that extends through said first axis of rotation of said first joint such that movement of said second link member with respect to said first link member is independent of movement of said tendons with respect to said first joint.

7. An articulated apparatus as claimed in claim 5, wherein said apparatus further includes a base portion including drive means for controlling the movement of each said link member with respect to other link members.

8. An articulated apparatus as claimed in claim 5, wherein said at least one tendon includes a cable having a diameter of about 80/1000 inch.

9. An articulated apparatus as claimed in claim 5, wherein at least one of said first, second and third link members may be inserted into a patient during endoscopic surgery.

10. An articulated apparatus comprising:

a first link member;

a second link member coupled to said first link member at a proximal end of said second link member by a first joint having a first axis of rotation; and a plurality of mutually independently longitudinally movable tendons each extending through said first axis of rotation of said first joint such that movement of said second link member with respect to said first link member is independent of longitudinal movement of said tendons with respect to said first joint, said tendons being movable in a longitudinal direction that is transverse to the first axis of rotation to effect movement of a plurality of distal link members that coupled to the distal end of said second link member.

11. An articulated apparatus as claimed in claim 10, wherein at least some of said serially coupled link members may be introduced into a patient during endoscopic surgery.

12. An articulated apparatus as claimed in claim 10, wherein said tendons each include a cable having a diameter of about 80/1000 inch.

13. An articulated apparatus as claimed in claim 10, wherein at least one of said link members may be inserted into a patient during endoscopic surgery.

14. An articulated apparatus comprising:

a first link member;

a second link member coupled to said first link member at a proximal end of said second link member by a first joint having a first axis of rotation; and a third link member coupled to a distal end of said second link member by a second joint, the movement of said third link member with respect to said second link member being governed by at least one tendon that passes through said first axis of rotation of said first joint such that movement of said at least one tendon with respect to said first joint does not cause movement of said second link member with respect to said first link member.

15. An articulated apparatus as claimed in claim 14, wherein said at least one tendon includes a cable having a diameter of about 80/1000 inch.

16. An articulated apparatus as claimed in claim 14, wherein at least one of said first, second and third link members may be inserted into a patient during endoscopic surgery.

17. An articulated apparatus comprising:

a first link member;

a second link member coupled to said first link member at a proximal end of said second link member by a first joint; and a third link member coupled to a distal end of said second link member by a second joint, the movement of said third link member with respect to said second link member being governed by at least one tendon that passes through said first joint such that movement of said second member with respect to said first member does not cause movement of said third member with respect to said second member, and such movement of said at least one tendon with respect to said first joint is independent of and does not cause movement of said second link member with respect to said first link member.

18. An articulated apparatus as claimed in claim 17, wherein said apparatus further includes a base portion including drive means for controlling the movement of each said link member with respect to other link members.

19. An articulated apparatus as claimed in claim 1, wherein said at least one tendon includes a cable having a diameter of about 80/1000 inch.

20. An articulated apparatus as claimed in claim 17, wherein at least one of said first, second and third link members may be inserted into a patient during endoscopic surgery.

21. An articulated apparatus as claimed in claim 17, wherein one of said link members comprises an end effector.

22. An articulated apparatus comprising:

a first link member;

a second link member coupled to said first link member at a proximal end of said second link member by a first joint having a first axis of rotation; and a plurality of mutually independently longitudinally movable tendons each extending through said first axis of rotation of said first joint such that movement of said second link member with respect to said first link member is independent of longitudinal movement of said tendons with respect to said first joint, said tendons being movable in a longitudinal direction that is transverse to the first axis of rotation to effect movement of at least a third link member that coupled to the distal end of said second link member.

23. An articulated apparatus as claimed in claim 22, wherein at least one of said link members may be inserted into a patient during endoscopic surgery.

* * * * *